United States Patent [19]

Brunswick

[11] Patent Number: 4,572,167
[45] Date of Patent: Feb. 25, 1986

[54] ORTHOPEDIC DEVICE AND PROCESS

[76] Inventor: Sumner Brunswick, 509 Ward St., Newton Centre, Mass. 02159

[21] Appl. No.: 539,545

[22] Filed: Oct. 6, 1983

Related U.S. Application Data

[63] Continuation-in-part of Ser. No. 247,622, Mar. 25, 1981, abandoned.

[51] Int. Cl.$^4$ .............................................. A61F 5/02
[52] U.S. Cl. ...................................... 128/78; 128/68; 2/44
[58] Field of Search ................ 128/DIG. 15, 136, 85, 128/89 R, 90, 68.1, 69, 78; 428/71, 76, 77, 314.4, 314.8

[56] References Cited

U.S. PATENT DOCUMENTS

| | | | |
|---|---|---|---|
| 4,019,505 | 4/1977 | Wartman | 128/90 |
| 4,193,395 | 3/1980 | Gruber | 128/90 |
| 4,226,230 | 10/1980 | Potts | 128/90 |
| 4,288,490 | 9/1981 | Alfter et al. | 428/314.8 |
| 4,357,725 | 11/1982 | Ahlm | 428/314.4 X |
| 4,360,984 | 11/1982 | Ruttenberg | 428/71 X |
| 4,474,840 | 10/1984 | Adams | 428/71 |
| 4,475,543 | 10/1984 | Brooks et al. | 128/89 R X |

OTHER PUBLICATIONS

Kydex Design and Fabrication Data, Rohm and Hass Brochure PL-674f.

*Primary Examiner*—Richard J. Apley
*Assistant Examiner*—Alan W. Cannon

[57] ABSTRACT

An improved orthopedic device for protecting and supporting a body portion has been developed. A structural support panel, moldable to the contours of the body portion at elevated temperatures while remaining substantially rigid and resilient at ambient temperature, is supported by a belt-like device which encircles the body portion. The belt-like device consists of a web adapted to encircle the body portion being supported formed of a resilient, stretchable material, a heat barrier which protects the body portion during molding of the structural support panel and a cinch strap for tightening the orthopedic device about the body portion. The heat barrier forms a pocket with the web which permits insertion of the structural support panel into the orthopedic device at elevated temperatures. The invention also includes a process for fitting the device to a body portion which provides maximum comfort for the patient because of its speed and accuracy. The structural support panel is molded directly to the body contours at elevated temperature and retains the molded shape as it cools. The invention promotes optimum support of the body portion in an inexpensive, removable brace or cast.

9 Claims, 7 Drawing Figures

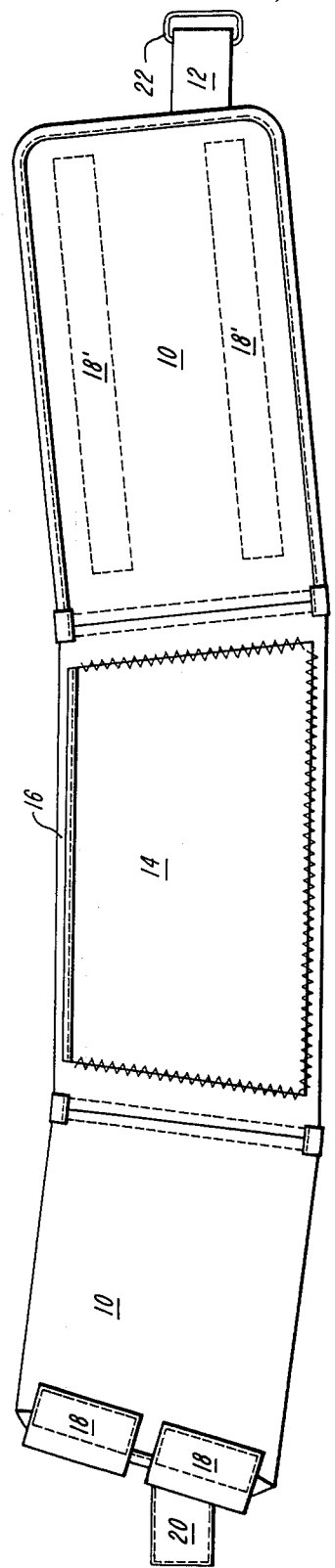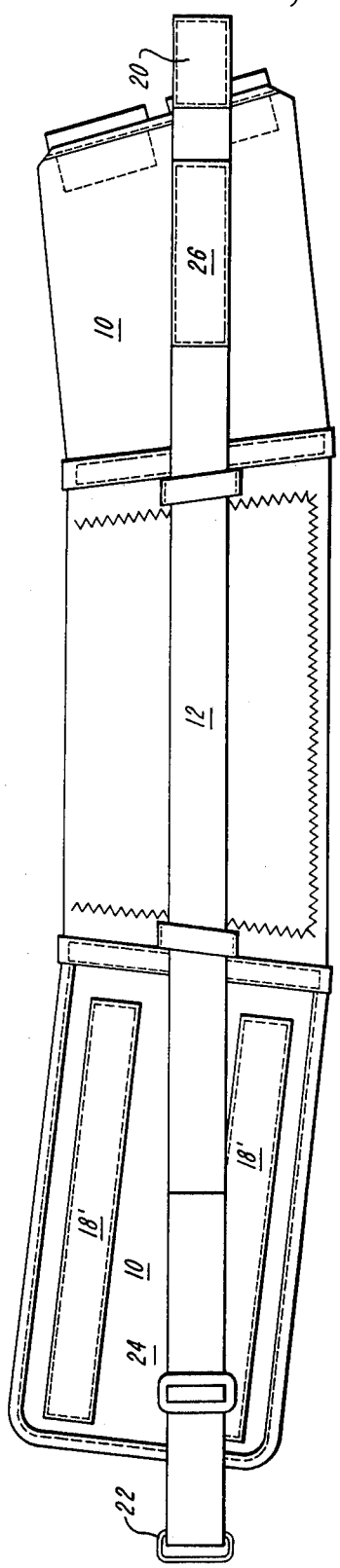

ORTHOPEDIC DEVICE AND PROCESS

REFERENCE TO RELATED APPLICATIONS

The present application is a continuation-in-part of co-pending application Ser. No. 247,622, entitled "Method and Apparatus for Thermoforming Orthopedic Support" filed Mar. 25, 1981 now abandoned, the disclosure of which is incorporated herein by reference.

BACKGROUND OF THE INVENTION

The present invention relates to orthopedic devices for supporting body portions and a method of fitting these devices. More particularly, the invention relates to inexpensive, easily formed, removable casts, braces or supports which provides comfortable patient fitting as well as providing better support and stability than previously available removable orthopedic supports.

Numerous materials have been used or proposed for orthopedic casts, splints, and braces. The conventional material is Plaster of Paris. Mixtures of Plaster of Paris and water are formable and moldable when wet but harden upon drying. Other materials which have been used for orthopedic supports include numerous synthetic resins, e.g., plastics. Some of these synthetic materials are soft for shaping and forming until subjected to a liquid polymer cure while others may cured by subjection to ultra-violet radiation. A large family of synthetic resins are thermoplastic; that is, they may be heat-softened and harden upon cooling. The following United States patents are examples of the orthopedic device art:

| U.S. Pat. No. | Patentee |
| --- | --- |
| 2,759,475 | Van Swaay |
| 2,781,757 | Hauser et al. |
| 2,800,129 | Van Swaay |
| 3,089,486 | Pike |
| 3,302,642 | Allen |
| 3,490,444 | Larson |
| 3,501,427 | Edenbaum |
| 3,662,057 | Webster et al. |
| 3,819,796 | Webster et al. |
| 3,998,219 | Mercer et al. |
| 4,006,741 | Arluck |
| 4,019,505 | Wartman |
| 4,226,230 | Potts |

The materials used for previous orthopedic devices such as casts, splints, and braces have significant shortcomings. For example, Plaster of Paris is inconvenient to use because it undergoes irreversible hardening and hence cannot be reformed. Casts made with Plaster of Paris are heavy and bulky, yet the material crumbles readily. Further, supports made of Plaster of Paris generally cannot be readily removed and replaced. Hence bathing with a Plaster of Paris cast causes problems because the plaster deteriorates when wet.

Other materials which have been used to form orthopedic supports also have physical properties which make them undesirable. For example, mixing of plastics to obtain polymerization for proper hardening often requires considerable care and undesirable clean-up. A number of materials are not easily moldable while others require cumbersome wrappings, e.g., with bandages, thereby prohibiting easy removal for bathing or comfort purposes.

Some previously used materials have additional difficulties because of insufficient strength, brittleness, dimensional instability, or lack of thermal softening satisfactory for forming directly on a limb or other body member to be supported. Many of the thermoplastic materials which have been suggested for use in orthopedic devices require molding temperatures so high that bulky, cumbersome thermal padding must be used to prevent damage to the skin.

Many other materials that are thermomoldable at lower temperatures lose their dimensional stability at too low a temperature to be useful. For example, one currently used brace, tradenamed WARM'N FORM, uses a thermoplastic sandwich such as disclosed in the Arluck U.S. Pat. No. 4,006,741. This thermoplastic sandwich can be molded simply by immersing in a hot water bath. This type of heating obviates the potential problem of blistering skin caused by too high a temperature but this brace has the problem that if it is left in a car on a hot day, the support member loses all dimensional stability and has to be remolded to conform to the body contours. This device also lacks sufficient structural support to properly protect the body portion.

Accordingly, an object of the invention is to provide an improved orthopedic device for protecting and supporting body portions such as limbs or torso. Another object of the invention is to provide an orthopedic device for supporting body portions which is easily fitted and moldable upon the patient without danger of injury. A further object of the invention is to provide a process for fitting an orthopedic device to a body portion which is quick, easy, and requires as little manipulation of the patient as possible. Fitting the device to the body portion in this manner is more comfortable for the patient and allows braces or other supports to be fitted and reformed as needed by lab technicians.

Other specific objects of the invention include the attainment of an orthopedic splint, brace, cast or like support that is easy to form, that can be thermoformed directly on the limb or other body portion to be supported after softening by dry heat, that can be formed with a relatively high degree of cleanliness and hence requires little clean-up, that is readily softened and may be resoftened to improve fit or accomodate changes in size of the body portion due to swelling, that is relatively comfortable for the patient to wear because of its light weight and proper support, that has a relatively high degree of dimensional stability after forming, that is sufficiently strong to resist crumbling, cracking, abrasion, and like breakage, that can be formed for relatively easy temporary removal and subsequent replacement, and that is highly resistant to water damage. Materials forming the orthopedic support should be compatible for long term contact with the patient. The orthopedic device of the present invention is versatile enough that it can be used to support almost any body portion, e.g., limbs or torso, yet is inexpensive and easy to mold.

Other objects and features of the invention will be apparent from the drawing and the following description.

SUMMARY OF THE INVENTION

This invention is based, in part, on the discovery that certain selected themoformable materials may be molded into a support panel having properties which permit construction of an improved orthopedic device. These materials provide satisfactory molding properties at elevated temperatures while retaining excellent strength, rigidity, and resiliency at room temperature.

When placed in properly designed supporting belts, support panels formed of these materials produce the improved orthopedic devices of the invention.

The purpose of the improved orthopedic device is to protect and support a body portion. The device includes a web adapted to encircle body portion to be supported and formed of a resilient, stretchable material. The web has interior and exterior surfaces, the interior closest to the body portion being supported. The device also includes a cinch strap adapted for tightening the device about the body portion and a heat barrier forming a pocket with the interior surface of the web to hold a structural support panel. Preferably, the heat barrier has an inner layer which contacts the body portion, a middle layer forming a thermal barrier and cushioning pad, and an outer layer which, together with the web, forms the surfaces of the pocket. Preferable materials include nylon for the inner layer, a polyether foam for the middle layer, and nylon adapted to withstand temperatures of up to about 400° F. for the outer layer. Most preferably, the three layers of the heat barrier are flame bonded.

The orthopedic device includes a structural support panel adapted to fit into the pocket formed by the heat barrier and the web. The structural support panel is formed of a material substantially flexible and moldable at forming temperatures of between about 220° F. and 375° F. while remaining substantially rigid, resilient and shape-retaining at ambient temperature. Preferred materials for the structural support are copolymers, blends, grafts, and alloys of acrylates, methacrylates, polycarbonates, and polyvinyl chlorides, most preferably an alloy of polyvinyl chloride and polymethylmethacrylate. Optimum structural support panels have a modulus of elasticity of about 100,000–500,000 psi at ambient temperature, and which falls to about 30–500 psi at forming temperatures. Most preferably, the structural support panel should be constructed of a material having a Rockwell R hardness of about 90, a Rockwell L hardness of about 45 and a Shore D Durometer hardness of about 75.

The invention also includes a process for fitting an orthopedice device to a body portion. The process starts by fitting a removable belt about the body portion. The belt is substantially similar to the orthopedic device as previously described except without the structural support panel; that is, the belt consists of a web, a cinch strap, and a pocket with a heat barrier on the inner side. After fitting the removable belt about the body portion, a thermoformable structural support panel, having properties previously described, is heated to between about 220° F. and 350° F. until the panel becomes pliable and substantially moldable. The heated support panel is then placed within the pocket of the belt with the belt on the body portion. The resilience or elasticity of the belt starts molding the support panel and pressure is applied to the exterior of the belt to enhance molding the support panel to conform to the body portion. The support panel is allowed to cool in place until the panel is rigid, resilient, and shape-retaining. Preferably, manual pressure is used to mold the support panel.

The process of the invention permits simple, quick, safe and reliable forming of the orthopedic support on a body portion. The discomfort normally experienced by a patient in fitting a brace is alleviated; in fact, the patient will normally feel a slight soothing warmth as the device is being molded. The device is readily removable which allows the patient to bathe or wash the body portion thereby promoting patient comfort. The support panel can be remolded in a very short time, e.g., about 5 minutes, which allows the device to be used to accomodate changes in size of the body portion, e.g., due to swelling, and permits ease of remolding the brace to the body portion for optimum patient comfort.

The following description and the drawing will further illustrate the efficacy of the invention.

BRIEF DESCRIPTION OF THE DRAWING

For a fuller understanding of the nature and objects of the invention, reference is made to the following detailed description and the accompanying drawing, in which:

FIG. 2 illustrates the interior surface of the back brace of FIG. 1;

FIG. 3 illustrates the exterior surface of the back brace of FIG. 1;

DESCRIPTION OF ILLUSTRATED EMBODIMENT

Figure 1:
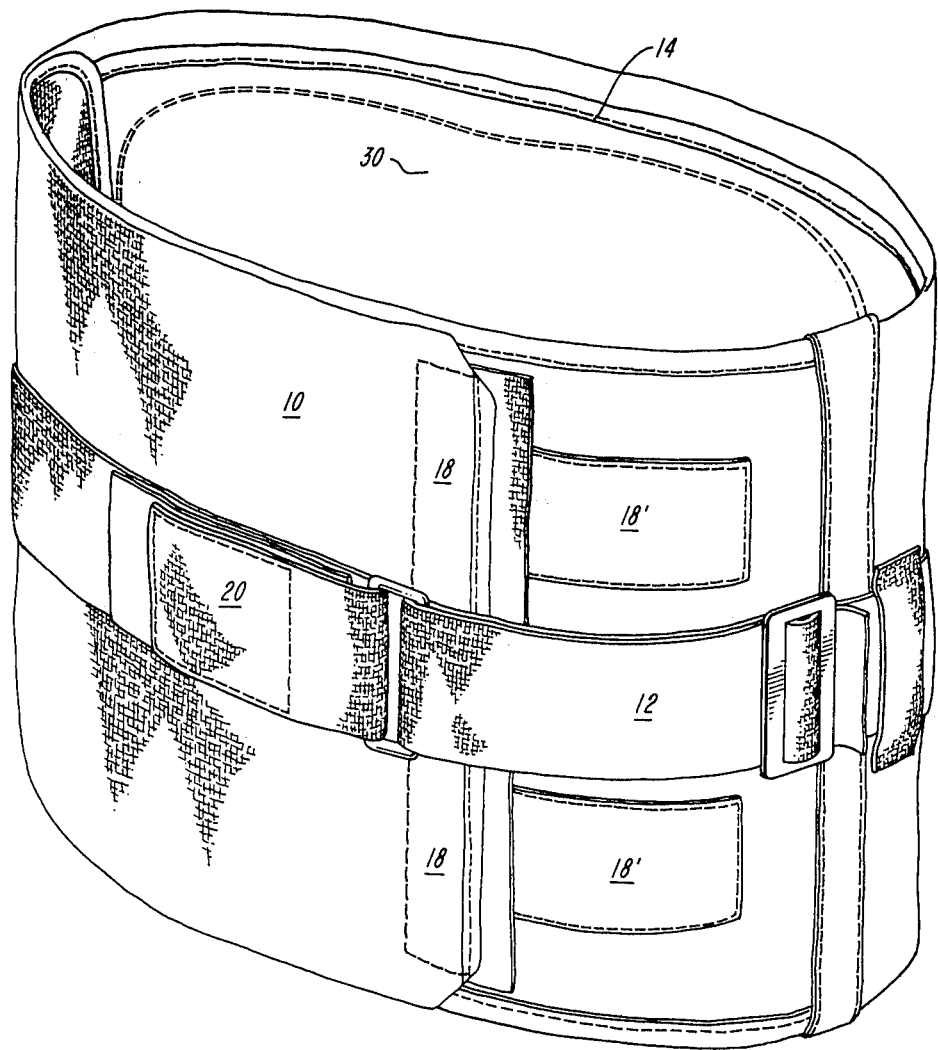
FIG. 1 is an illustration of an orthopedice device within the scope of the invention, specifically a lumbosacral back brace.

The present invention features an orthopedic device and a process for fitting the orthopedic device to a body portion. Depending on the support requirements of the body portion encircled by the orthopedic device, the size of the structural support panel and, accordingly, the shape and size of the thermal barrier varies. For example, if the orthopedic device is to be used to support a limb, the structural support should almost completely encircle the limb, only having an opening sufficient that the support may be removed for bathing or examination. If, however, the orthopedic device is used as a support for the back, the structural support panel does not need to encircle the body but rather can be molded to the contours of the back and hips.

As previously noted, a number of different materials can be used for the structural support panel. These materials include alloys, grafts, blends, and copolymers of polycarbonates, acrylates, methacrylates, and polyvinyl chlorides. The major requirements for materials forming the structural support panel are durability, scuff resistence, rigidity, resilience and shape-retaining properties at ambient temperature while being thermomoldable and substantially flexible at elevated temperatures. The support material is, moreover, to retain its perimeter shape at the elevated molding (fitting) temperature. Thermoplastic resins having a modulus of elasticity of about 100,000–500,000 psi at room temperature of requirements and a modulus of elasticity of 30–500 psi at forming temperatures of about 220° F. to 375° F. fulfill other materials requirements. Preferably, materials used for the structural support have a Rockwell R hardness of about 90, a Rockwell L hardness of about 45 and Shore D Durometer hardness of about 75.

The structural support material should be thermoformable at temperatures of not less than about 220° F. but not more than about 375° F. If the material has substantial moldability at temperatures less than 220°, it may not not hold its shape if placed in hot areas, e.g., a car trunk, while if the material requires a much higher temperature for moldability, the danger of burning the patient or the person molding the brace is great. One material which has been used successfully for the structural support panel is an alloy of polymethylmethacrylate and polyvinyl chloride produced by Rohm and Haas called KYDEX. This material, the exact formulation of which is kept a trade secret by Rohm and Hass, is believed to be a true solution of polyvinyl chloride and polymethylmethacrylate. Attached hereto as Appendix I is a copy of a product specification brochure for the Kydex material. The Kydex polymer has a Shore D Durometer hardness of 77, a Rockwell R hardness of 90 and a Rockwell L hardness of 45. Its modulus of elasticity at room temperature is about 330,000 psi while at 350° F., the modulus of elasticity drops to about 80 psi. Kydex also has a tensile yield of about 6000 psi on the D-638 scale and is substantially scuff resistant. While the Kydex polymer appears to be an excellent material for the structural support, those skilled in the art will be able to determine other materials which also are well suited.

The following illustrated embodiment further explains the invention and its efficacy. This embodiment is a lumbosacral brace to support the back, particularly at the S-1, S-2 and L-4, L-5 area.

Turning to the drawing, FIG. 1 illustrates a lumbosacral brace in a closed position as if encircling a body. The brace has four major portions: a web 10 formed of a resilient, elastic material such as conventional three panel elastic, a cinch strap 12 formed, preferably, of a non-stretchable material, a heat barrier 14 which together with web 10 forms a pocket 16 and a structural support panel 30 formed of a material like Kydex. Support panel 30 is shown in FIG. 1 only as cross-hatching since it would not be seen from this perspective. The other figures further illustrate this brace and its parts.

A description of the process for fitting a brace about a body portion, e.g., the lumbosacral region, further illustrates the invention. The body is first encircled by the orthopedic device without structural support panel 30 in place. FIG. 2 illustrates the interior portion of the belt section of the device, that which is placed closest to the body, while FIG. 3 shows the exterior. Heat barrier 14, which forms pocket 16 with web 10, is placed against the body section to be supported and web 10 encircles the front of the patient with the left portion closing first. Web 10 is fitted in place by adjustable closing devices 18 and 18', preferably Velcro brand hook and loop fastening device strips, on the two side panels of web 10. Once a rough adjustment is made with closing devices 18 and 18', cinch belt 12 is tightened about web 10. Cinch strap 12 has its own two-part adjustable closing device, again preferably Velco, designated 20 and 26, which is used to obtain a rough approximation of the final fit. The actual tightening is done by passing cinch strap 12 through buckle 24 to achieve proper tightening. Once the proper adjustment of cinch strap 12 through buckle 24 has been made, all opening and closing of cinch strap 12 is carried out using Velcro closing device 20 and 26.

Figure 5:
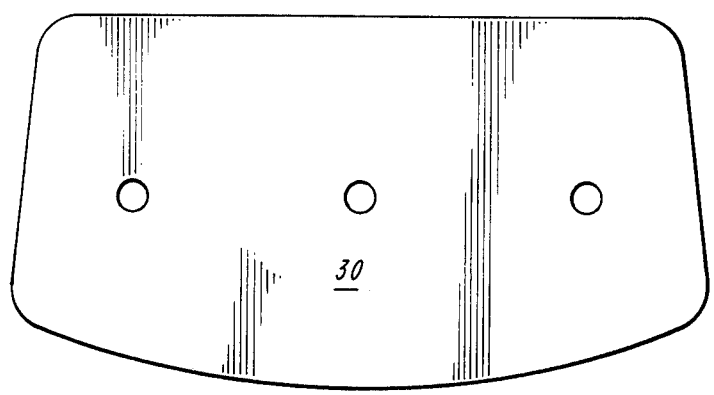
FIG. 5 illustrates a blank for molding into a structural support panel.
Figure 6:
FIG. 6 illustrates a side view of the blank illustrated in FIG. 5.
Figure 7:
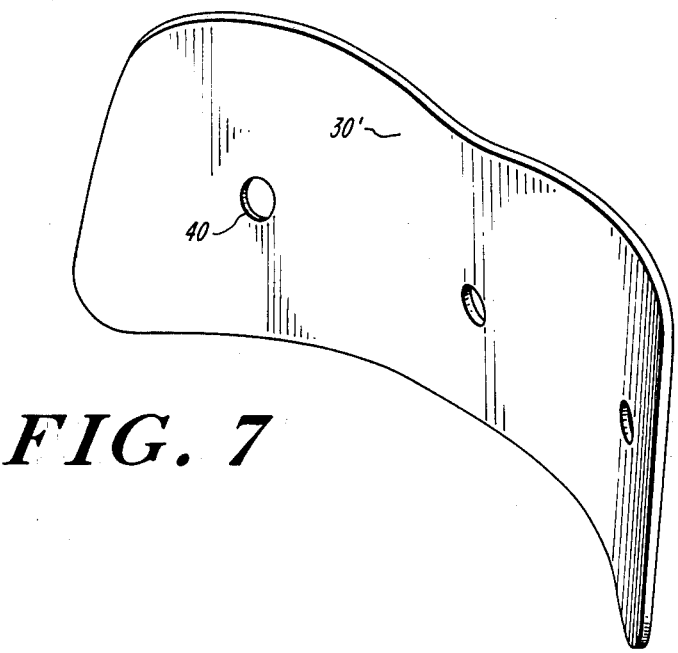
FIG. 7 illustrates a structural support panel for a back brace as molded from the blank of FIGS. 5 and 6.

While the belt portion of the orthopedic device is being fitted, structural support panel 30 can be heated to molding temperature. One procedure which has been used successfully consists of placing a blank or preformed panel 30 such as is illustrated in FIGS. 5 and 6 on a dry heat device, e.g., a hot plate or warming tray, until flexible, approximately 5-10 minutes. At molding temperatures of 220° F.-375° F., structural support panel 30 is quite flexible; a mitten or glove is typically used for handling of this temperature. Structural support panel 30 is placed in pocket 16 formed by heat barrier 14 and web 10 and the device is quickly placed about the patient's body in proper position. Cinch 12 is tightened and locked about the patient with Velcro closing device 20 and 26. Tightening the device about the patient starts the molding process; that is, the elastic of the web partially molds the support panel to the body portion. The warm and moldable structural support panel 30 is normally hand molded to enhance the conforming of the brace to the shape of the body portion. Once structural support panel 30 is cool, normally a period of about 5 minutes, structural support panel 30 is rigid, with stiff resilience and shape-retaining. FIG. 7 illustrates a structural support panel 30' which has been molded to conform to the lumbosacral section of a back. During the fitting process for this type of brace, the patient has a minimum of discomfort and normally feels a slight warmth which is pleasant and soothing. After the molding process is finished, the brace is ready to wear.

Figure 4:
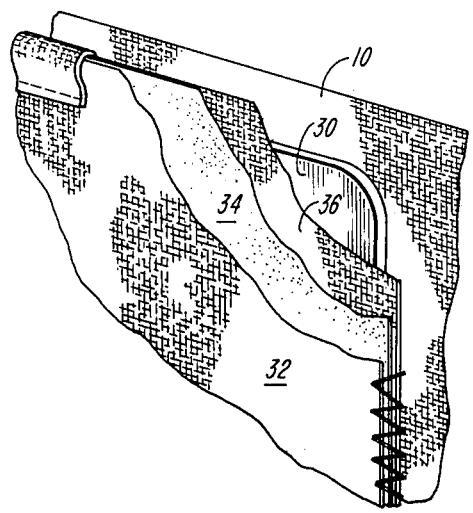
FIG. 4 shows a cutaway view of the pocket section of the brace illustrated in FIG. 1 with a support panel in place, particularly illustrating the layers of the preferred heat barrier.

FIG. 4 illustrates the heat barrier and pocket of the orthopedic device. Preferably, the heat barrier consists of three layers: an inner layer 32, a middle layer 34 formed of an insulating material which acts as a thermal barrier, and an outer layer 36 which forms one surface of pocket 16. Inner layer 32 is preferably made of nylon, e.g., a nylon tricot, and is placed next to the patient's skin or clothing. Middle layer 34 can be any insulating material but preferably is a thin (e.g., less than ⅛ inch thick) cushioning foam such as conventional polyether foam which has sufficient thermally insulating properties to allow the device to be placed directly against the patient's skin after the heated structural support panel is placed within pocket 16. Outer layer 36 must be relatively heat resistent since it is in direct contact with heated structural support panel 30. Preferably, outer surface 36 is a nylon which can withstand temperatures of 400° F. FIG. 4 also shows how structural support panel 30 is placed between outer layer 36 and web 10 in pocket 16. As shown, exterior surfaces of the panel are openly exposed to the opposed surfaces of the pocket. Panel 30 is illustrated with several ventilation holes 40 which permit air cooling while patient wears the brace. Normally, pocket 16 is sewn on three sides as illustrated in FIGS. 2 and 3 with only the top open, but another orientation of pocket 16 which will allow easy insertion of structural support panel 30 may be employed. The exact choice of materials for the belt is within the knowledge of those skilled in the art. Belts fitting these specifications may be manufactured by various venders; in fact, belts for a commercial version of the present invention, tradenamed ORTHO-MOLD TM, are available from Brunswick Medical of Boston, Massachusetts.

The orthopedic device disclosed herein allows quick, easy fitting with maximum comfort to the patient and maximum support while being removable, easily remoldable and easily cleanable. The orthopedic device of the present invention yields superior patient comfort and is reasonable in cost to form and fabricate. It is thus seen that the objects set forth above are efficiently attained by the disclosed invention.

The process and device of the invention can be modified in ways obvious to those skilled in the art. Accordingly, the invention includes such modifications and variations.

What is claimed is:

1. An improved orthopedic device for protecting and supporting a body portion, said device comprising
   A. a web member having interior and exterior surfaces and comprising a resilient stretchable material and adapted to encircle a body portion,
   B. a cinch member adapted for tightening the device about said body portion,
   C. a pliable heat barrier attached to the interior surface of said web member and forming a pocket with said web member and having opposed pocket surfaces, and
   D. a preformed structural support panel adapted to removalby and replaceable fit into said pocket, said panel being of a material which is thermoformable at forming temperatures of between 220° F. and 375° F. and being substantially rigid and shape-retaining at ambient temperatures, said material being selected from a group consisting of copolymers, blends, grafts and alloys of acrylates, methacrylates, polycarbonates and polyvinyl chlorides, and wherein surfaces of said panel formed by said material are, when said panel is within said pocket, openly exposed to said opposed pocket surfaces.

2. The orthopedic device of claim 1 wherein said material comprises an alloy of polyvinyl chloride and polymethylmethacrylate.

3. The orthopedic device of claim 1 wherein said material has a modulus of elasticity of about 100,000–500,000 psi at ambient temperatures and about 30–500 psi at forming temperatures.

4. The orthopedic device of claim 1 wherein said material has a Rockwell R hardness of about 90, a Rockwell L hardness of about 45, and a Shore D Durometer hardness of about 75.

5. A process for fitting an orthopedic device to a body portion, said process comprising the steps of
   A. fitting a removable belt about the body portion, said belt comprising
      i. a web member having interior and exterior surfaces and comprising a resilient, stretchable material and adapted to encircle the body portion,
      ii. a cinch member adapted for tightening the device about said body portion, and
      iii. a heat barrier attached to the interior of said web member and forming a pocket with said web member and having opposed pocket surfaces,
   B. heating a preformed thermoformable support panel to a temperature of between 200° F. to 375° F. whereat said support panel becomes pliable and substantially moldable,
   C. inserting said heated, thermoformable support panel with said pocket with heated surfaces of said panel openly exposed to said opposed pocket surfaces,
   D. applying pressure to said support panel through the exterior of said web to enhance molding said support panel to conform to said body portion, and
   E. allowing said support panel to cool until said support panel is rigid and shape-retaining.

6. A process according to claim 5 further characterized by the step of constituting said support panel of a material selected from the group consisting of copolymers, blends, grafts, and alloys of acrylates, methacrylates, polycarbonates and polyvinyl chlorides.

7. A method according to claim 5 further characterized by the step of constituting said panel of an alloy of polyvinyl chloride and polymethylmethacrylate.

8. A process for fitting an orthopedic device to a body portion, said process comprising the steps of
   A. providing a removable body belt comprising
      (i) a web member having interior and exterior surfaces and comprising a resilient, stretchable material and adapted to encircle a body portion,
      (ii) a cinch member adapted for tightening the device about said body portion, and
      (iii) a heat barrier attached to the interior of said web member and forming a pocket with said web member and having opposed pocket surfaces,
   B. heating a preformed thermoformable support panel to a temperature of between 200° F. to 375° F. whereat said support panel is pliable and substantially moldable,
   C. inserting said heated, thermoformable support panel within said pocket with heated surfaces of said panel exposed to said opposed pocket surfaces,
   D. fitting said belt with said heated panel in said pocket thereof around a body portion,
   E. conforming said pocket-carried heated panel, at least in part by pressure of said belt against said body portion, to the body portion which said panel overlies, and
   F. allowing said support panel to cool within said pocket until said support panel is rigid and shape-retaining.

9. A process according to claim 8 comprising the further steps of
   A. removing said support panel from said pocket and reheating said support panel to be moldable, and
   B. reforming said reheated panel, after reinsertion into said pocket, further into conformity with the body portion.

* * * * *